United States Patent [19]

Lawrence

[11] Patent Number: 5,053,342

[45] Date of Patent: Oct. 1, 1991

[54] FECAL OCCULT BLOOD TEST REAGENTS

[75] Inventor: Paul J. Lawrence, Campbell, Calif.

[73] Assignee: Litmus Concepts, Inc., Santa Clara, Calif.

[21] Appl. No.: 520,088

[22] Filed: May 7, 1990

Related U.S. Application Data

[63] Continuation of Ser. No. 138,496, Dec. 24, 1987, Pat. No. 4,939,097, which is a continuation-in-part of Ser. No. 869,573, Jun. 2, 1986, abandoned, which is a continuation-in-part of Ser. No. 680,357, Dec. 11, 1984, Pat. No. 4,615,982.

[51] Int. Cl.$^5$ ............................................. G01N 33/49
[52] U.S. Cl. ...................................... 436/66; 422/56; 422/57; 422/58; 435/28; 436/904
[58] Field of Search ............... 422/56, 57, 58; 436/66, 436/904; 435/28

[56] References Cited

U.S. PATENT DOCUMENTS

| | | |
|---|---|---|
| 2,290,436 | 7/1942 | Kamlet . |
| 3,092,464 | 7/1963 | Adams et al. . |
| 3,236,850 | 2/1966 | Oswald et al. . |
| 3,290,117 | 12/1966 | Adams et al. . |
| 3,721,607 | 3/1973 | Gruber et al. . |
| 3,876,631 | 4/1975 | Hawkins . |
| 3,917,452 | 11/1975 | Werner et al. . |
| 3,932,528 | 1/1976 | Suda et al. . |
| 3,975,161 | 8/1976 | Svoboda et al. . |
| 3,986,833 | 10/1976 | Mast et al. . |
| 3,996,006 | 12/1976 | Pagano et al. . |
| 4,017,261 | 4/1977 | Suoboda et al. ........................ 422/56 |
| 4,063,894 | 12/1977 | Ogawa et al. .......................... 422/56 |
| 4,071,317 | 1/1978 | Lam . |
| 4,088,642 | 5/1978 | Sheppard et al. . |
| 4,115,419 | 9/1978 | Naglieri et al. . |
| 4,148,611 | 4/1979 | Nand et al. . |
| 4,202,829 | 5/1980 | DeLucca et al. . |
| 4,333,734 | 6/1982 | Fleisher . |
| 4,386,053 | 5/1983 | Motobayashi . |
| 4,481,295 | 11/1984 | Habenstein . |
| 4,556,640 | 12/1985 | Gantzer . |
| 4,578,359 | 3/1986 | Oksman et al. . |
| 4,596,770 | 6/1986 | Parham et al. . |
| 4,615,982 | 10/1986 | Lawrence ............................. 422/56 |
| 4,818,702 | 4/1989 | Lawrence . |
| 4,820,646 | 4/1989 | Lawrence . |
| 4,937,197 | 6/1990 | Lawrence . |
| 4,939,097 | 7/1990 | Lawrence . |
| 4,942,132 | 7/1990 | Lawrence . |
| 4,971,914 | 11/1990 | Lawrence . |

OTHER PUBLICATIONS

H. S. Banyal et al, *Life Sciences*, 31:1141-1144 (1982).
Berezin et al., *Chem. Abstracts*, vol. 103, No. 76969p (1985).
B. Bhattacharyya et al., *Biochemical Pharmacology*, 32(19):2965-2968 (1983).
G. Blauer, *Arch. Biochem. Biophys.*, 251(1):306-314 (1986).
A. C. Chou et al., *Biochemistry*, 19:1543-1549 (1980).
A. C. Chou et al., *J. Clin. Invest.*, 66:856-858 (1980).
S. N. Cohen and K. L. Yielding, *J. Biol. Chem.*, 240(7):3123-3131 (1965).
P. Dutta et al., *J. Pharmacol. and Exper. Therap.*, 225(3):729-734 (1983).
N. L. Etkin and J. W. Eaton, "Malaria-Induced Erythrocyte Oxidant Sensitivity", in *Erythrocyte Structure and Function*, New York: Alan R. Liss, Inc., 1975.
C. D. Fitch et al., "Ferriprotoporphyrin IX: A Mediator of the Antimalarial Action of Oxidants and 4-Aminoquinoline Drugs", in *Malaria and the Red Cell*, (New York: Alan R. Liss Inc., 1984), pp. 119-130.
C. D. Fitch et al., *Antimicrob. Agents and Chemother.*, 21(5):819-822 (1982).
C. D. Fitch, "Mode of Actio of Antimalarial Drugs", in *Malaria and the Red Cell*, (London: Ciba Foundation Symposium94, 1983), pp. 222-232.
H. Foy and A. Kondi, *Annals of Trop. Med. Parasitol.*, 44:309-318 (1950).
D. M. Fraser and W. O. Kermack, *Brit. J. Pharmacol.*, 12:16-23 (1957).
U. Gerlach, *Klin. Wschr.*, 36:376-378 (1958).
F. E. Hahn, in *Antibiotics: Mechanism of Action of Antimicrobial and Antitumor Agents*, vol. 3, pp. 58-78, ed. Corcoran et al., West Berlin: Springer-Verlag, 1974.
S. K. Janney et al., *Blood*, 67(2):331-333 (1986).
A. Jearnpipatkul et al., *Experientia*, 36:1063-1064 (1980).
A. Jearnpipatkul et al., *Chem. Biol. Interactions*, 33:83-90 (1980).
D. J. Krogstad et al., *Am. J. Trop. Med Hg.*, 36(2):213-220 (1987).
H. Laser et al., *Parasitology*, 71:167-181 (1975).
P. B. Macomber and H. Sprinz, *Nature*, 214:937-939 (1967).
S. Moreau et al., *Biochimie*, 64:1015-1025 (1982).
S. Moreau et al., *Biochim. Biophys. Acta.*, 840:107-116 (1985).
S. V. Otton et al., *Experientia*, 40:973-974 (1984).
B. Panijpan et al., *Bioscience Reports*, 3:1113-1117 (1983).
Schwartz et al., *Clinical Chemistry*, vol. 29, No. 12, pp. 2062-2067.
J. K. Shute et al., *Biochem. Pharmacol.*, 34:2471-2475 (1985).
P. M. L. Siu, *Comp. Biochem. Physiol.*, 23:785-795 (1967).
D. L. Vander Jagt et al., *Molecular and Biochemical Parasitology*, 10:45-54 (1984).
D. C. Warhurst, *Biochemical Pharmacology*, 30(24):3323-3327 (1981).

*Primary Examiner*—Robert J. Warden
*Assistant Examiner*—Lyle A. Alexander
*Attorney, Agent, or Firm*—Dianne E. Reed

[57] ABSTRACT

An improved method for detecting peroxidatively active materials in a sample is provided, the method incorporating antimalarial drugs such as quinine, quinidine, chloroquine, primaquine, and quinacrine as modulating compounds. In a preferred embodiment, the method is a fecal occult blood test (FOBT), in which a fecal specimen is contacted with a chromogen and a hydroperoxide in the presence of a selected quinoline derivative. The method enables careful modulation of test sensitivity and specificity, and further provides an FOBT in which interference from dietary meat ingestion is substantially eliminated.

18 Claims, No Drawings

FECAL OCCULT BLOOD TEST REAGENTS

CROSS-REFERENCE TO RELATED APPLICATIONS

This application is a continuation of U.S. patent application Ser. No. 07/138,496, filed Dec. 24, 1987, now U.S. Pat. No. 4,939,097, which is a continuation-in-part of PCT Application No. US87/01271 and U.S. patent application Ser. No. 06/869,573, filed June 2, 1986, now abandoned, which in turn is a continuation-in-part of U.S. patent application Ser. No. 06/680,357, filed Dec. 11, 1984, now U.S. Pat. No. 4,615,982, and PCT Application No. US85/02446, filed Dec. 10, 1985.

DESCRIPTION

1. Technical Field

This invention is in the field of fecal occult blood tests (FOBT). More particularly it relates to improved FOBT that provide a reduced incidence of false results and/or greater sensitivity and specificity and/or are easier to perform.

2. Background Art

FOBT are commonly used clinically to detect occult blood loss from gastrointestinal (GI) lesions. For example, carcinoma of the colon and rectum is the most serious cancer in the U.S. and second only to lung cancer in causing death—approximately 100,000 new cases and 50,000 deaths annually. Because colorectal cancer is slowly progressive with a long asymptomatic period, it provides an ideal opportunity for early detection and successful therapy. Thus, FOBT are a rational attempt at early diagnosis because the colorectal lesions frequently bleed, and routine noninvasive testing is possible. Similarly, hospitals and physicians very often utilize FOBT to detect or monitor GI lesions resulting from disease, injury, surgery, and other causes.

Early FOBT involved shipping entire 24–48 hour fecal collections in paint cans to central laboratories for testing with an acidified guaiac solution and hydrogen peroxide. Guaiac is a complex plant extract containing the leuco dye, alpha guaiaconic acid. Leuco dyes are oxidized by hydroperoxides in the presence of catalyst to form a blue color:

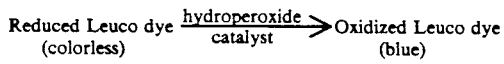

Reduced Leuco dye $\xrightarrow{\text{hydroperoxide}}_{\text{catalyst}}$ Oxidized Leuco dye
(colorless) (blue)

Because hemoglobin is an efficient catalyst (pseudoperoxidase), feces may be tested for occult blood using a leuco dye/hydroperoxide reagent. Nonetheless, the procedure remained very poorly utilized because of the disagreeable nature of the test and physicians were largely denied this very useful information.

U.S. Pat. No. 3,996,006 describes a FOBT technique that popularized the guaiac-based test for occult blood in feces. It employs a slide having a sheet of guaiac-impregnated paper between a front panel and a rear panel with openings in the panels and pivotal flaps to cover the openings. A fecal specimen is placed on the paper through the opening in the front panel and that panel is closed. The rear panel is then opened and a hydrogen peroxide developer is placed on the paper via the opening in the rear panel. If blood is present in the specimen, the paper will turn blue. A commercial embodiment of this test, called the HEMOCCULT ® test, is widely used in hospitals and physicians' offices.

Despite the widespread popularity of the HEMOCCULT ® test, recent studies have pointed out serious limitations in its sensitivity and specificity. As discussed in U.S. Ser. No. 869,573, the parent application hereto (the disclosure of which is incorporated by reference herein), applicant believes that the sensitivity limitation is due partly to (1) the fact that hemoglobin in many specimens is degraded to derivatives that exhibit little or no peroxidative activity, (2) degradation of peroxidatively active hemoproteins by the hydroperoxide reagent used in the test and (3) the relative insolubility of the degraded products (i.e., iron protoporphyrins such as heme and hemin) in the reagents used in the test. Sensitivity limitations, of course, may cause false negative results. The specificity limitation is probably due to the response of the test to plant peroxidases, residual fecal iron protoporphyrins from dietary meat ingestion and/or iron or copper in the specimens or the environment in which the test is run. Specificity limitations lead to false positive results.

U.S. Pat. No. 4,333,734 describes a variation in the guaiac-based FOBT that is intended to reduce the incidence of false positive results due to the presence of plant peroxidases in the specimen. It includes a peroxidase denaturing agent such as urea or guanidine hydrochloride together with a metal chelating agent to sequester calcium and magnesium ions that are essential to peroxidase activity. The denaturant and the chelating agent are formulated with the guaiac.

U.S. Pat. No. 4,071,317 relates to using polar solvents such as dimethyl sulfoxide (DMSO) and dimethyl formamide (DMF) to stabilize mixtures of organic hydroperoxides and leuco dyes that are used in FOBT. The solvent is formulated in minor proportions with the hydroperoxide and leuco dye. This solution is applied to a solid matrix and the matrix is dried prior to use in testing.

Several references indicate that monomeric species of iron protoporphyrins exhibit greater peroxidase activity than dimeric or aggregated species. Biochem J (1970) 117: 741–744; Biochem J (1973) 135: 353359; Biochem J (1976) 153: 279–285; and Biochemistry (1974) 13: 4279–4284. Biochem J (1979) 179: 281–289 indicates that hemin occurs in its monomeric form in mixtures of DMSO and water that contain in excess of about 35% (v/v) DMSO.

Biochem J (1968) 108: 131–136 discusses the solubility of nitrogenous ligand-alkaline hematin complexes. Biochimica et Biochysica Acta (1977) 498: 205–214 describes the use of various water-soluble polymers such as polyethylene oxide, polyvinyl alcohol, polyvinyl pyrrolidone, and polystyrene sulfonate to dissolve aggregates of ferroheme and protoporphyrin in alkaline aqueous media.

The primary object of the invention described in the parent application hereto was to reduce the incidence of incorrect results (both false positive and false negative) in leuco dye-based FOBT. This was achieved, as described in that application, by applying a hydroperoxide or both a hydroperoxide and a leuco dye to the specimen in a solution that uses a solvent system that dissolves iron protoporphyrins.

The present invention represents an improvement over the FOBT known in the art as well as over the FOBT described in the parent application hereto. Specifically, the present invention provides for: (1) acceleration of color formation and enhancement of the total color produced; and (2) enhancement of test sensitivity and specificity, the latter effected by inhibition of the activity of endogenous fecal hemes present as a result of dietary meat ingestion. The present method and reagent composition accomplishes the aforementioned objects by inclusion of one or more modulating compounds which regulate peroxidative activity.

DISCLOSURE OF THE INVENTION

One aspect of the invention is thus an improved method for detecting the presence of a peroxidatively active substance in a sample by contacting the sample with a chromogen and a hydroperoxide, the improvement comprising applying to the sample, along with the chromogen and the hydroperoxide, a modulating compound selected from the group consisting of chloroquine, quinacrine, quinine, primaquine, quinidine, and mixtures thereof.

Another aspect of the invention is a developer composition comprising a hydroperoxide and a modulating compound selected from the group consisting of chloroquine, quinacrine, quinine, primaquine, quinidine, and mixtures thereof. The developer composition is useful (in conjunction with a chromogen) in colorimetrically detecting peroxidatively active substances.

Still another aspect of the invention is a complete reagent composition for use in detecting the presence of a peroxidatively active substance in a sample, comprising a chromogen, a hydroperoxide, and a modulating compound selected from the group consisting of chloroquine, quinacrine, quinine, primaquine, quinidine and mixtures thereof.

In a preferred embodiment, the method for detecting the presence of a peroxidatively active substance in a sample is a fecal occult blood test (FOBT) in which a chromogen and a hydroperoxide are used to detect hemoproteins in a fecal specimen. The aforementioned modulating compounds which, according to the present method, are included in such a test, are antimalarial drugs which either accelerate or inhibit the colorimetric reaction that is the basis of the test. The "accelerators" include chloroquine and quinacrine, while the "inhibitors" include quinine, primaquine and quinidine.

It has surprisingly been found by the inventor herein that these antimalarial drugs can be used to modify heme redox catalysis and thus modulate the sensitivity and specificity of colorimetric tests such as those described in the parent application hereto. Specifically, in an FOBT wherein a chromogen and a hydroperoxide are used in combination in order to detect hemoproteins, i.e., by virtue of the peroxidative activity of various hemoproteins in catalyzing the oxidation of the chromogen to a colored state, the accelerator compounds disclosed herein accelerate the rate of color formation and enhance the total color produced, while the inhibitors actually inhibit the rate and extent of color formation. The accelerators and inhibitors may thus be used together or individually to modulate the rate, sensitivity and specificity of these tests.

MODES FOR CARRYING OUT THE INVENTION

As used herein the term "hemoprotein" is intended to include hemoglobin and derivatives of hemoglobin such as heme, hemin and hematin that have the ability (particularly in their monomeric form) to catalyze the oxidation of a chromogen by a hydroperoxide to cause the chromogen to be oxidized and thereby produce a detectable response. Such ability is sometimes referred to herein as "peroxidative activity".

As used herein the term "chromogen" is not intended to be limited to a particular chemical species or genus but is intended to encompass indicators and mixtures of indicators that produce a detectable response, typically a color change that is visible to the naked eye. Particularly preferred examples of chromogens are leuco dyes such as guaiac, benzidine, o-toluidine, cresol, catechol, 3,3',5,5'-tetramethylbenzidine, p-toluidine, betanaphthol, pyrogallol, o-phenylenediamine, leuco malachite green, 3-amino ethylcarbazole, 4-amino antipyrine, phenol, 2,2'-azino-di-(3-ethylbenzyl)azoline sulfonic acid (ABTS), and mixtures thereof.

In its broadest sense, the invention is directed to an improved method for detecting the presence of a peroxidatively active substance in a sample, comprising contacting the sample with a chromogen, a hydroperoxide, and a modulating compound selected from the group consisting of chloroquine, quinacrine, quinine, primaquine, quinidine, and mixtures thereof. The invention is also directed (1) to a developing composition containing the hydroperoxide and the aforementioned modulating compound in a solution containing a solvent for iron protoporphyrins, and (2) to a complete reagent composition which contains the developing composition as well as the chromogen.

In a preferred embodiment, the method for detecting the presence of a peroxidatively active substance in a sample is a fecal occult blood test (FOBT). In such an embodiment, as noted earlier, various iron protoporphyrin compounds present in the sample will act to catalyze the oxidation of the chromogen, in the presence of a hydroperoxide, to a colored state.

While any number of chromogens may be used which will produce the desired colorimetric reaction upon oxidation, preferred chromogens for use herein are guaiac and ABTS, and a particularly preferred chromogen is a mixture of guaiac and ABTS. This latter mixture provides enhanced color, thus improving test sensitivity and specificity. That is, the mixture produces a color response that is greater than the sum of the responses that would be expected from the individual components. In addition to enhanced color intensity, the color is spread more evenly than that observed in current FOBT (e.g., the HEMOCCULT® test), is more stable (i.e., long-lasting), and is more reproducible. The weight ratio of guaiac to ABTS in the mixture will be in the range of about 1:5 to about 5:1, preferably approximately 1:1. When the chromogen mixture is formulated as a complete reagent with a peroxide and/or in a solvent for iron protoporphyrins as will be discussed, it is preferable to include a stabilizing amount of sodium sulfite or other antioxidant in the formulation. Preferably, the sodium sulfite is present in amounts in excess of that which saturates the solution. The concentration of the chromogen mixture in solution will usually be in the range of about 0.05 to about 10%.

As described in the parent application hereto, the chromogen or chromogen mixture may be used in various FOBT formats that involve contacting a fecal specimen placed on a solid test matrix with a leuco dye and a hydroperoxide. In one format the matrix is impregnated with the mixture (i.e., the matrix carries the mixture in dry form) beforehand. In another the matrix is impregnated with one of the components of the mixture and the other is applied in solution to the matrix/specimen either combined with or separately from the hydroperoxide. For long-term stability, it is preferred to keep the chromogen mixture and hydroperoxide separate. For instance, they might be packaged in separate containers adapted for simultaneous dispensing, such as a double-barreled syringe with a common outlet nozzle. Another format is to employ the chromogen in solution as part of a complete reagent composition (when long-term stability is not involved). The complete reagent composition contains, in addition to the chromogen and the solvent, a hydroperoxide and, optionally, other additives such as hemoprotein solubilizing agents, stabilizers, vegetable peroxidase inhibitors, iron chelators, accelerators, and buffers. Such additives may, of course, be impregnated into the solid test matrix in the other test formats. Use of such a complete reagent composition has the advantages of avoiding the need to impregnate the matrix beforehand, permitting new test geometries, lower manufacturing costs and use of untreated matrices, and improved test performance.

The application to the fecal specimen of a developer/complete reagent composition having a solvent system based on a solvent for iron protoporphyrins may also be used in a variety of FOBT formats. When used as a developer, the solution will contain the hydroperoxide and be applied to the specimen on a leuco dye-impregnated matrix. When used in the form of a complete reagent, the solution will contain a leuco dye, preferably the multi-chromogen of the invention, together with the hydroperoxide and, optionally, other additives such as those described above.

The test matrices used in the FOBT methods of the invention may be made from a variety of porous materials such as cellulosics (wood, paper), ceramic, glass fibers, natural or synthetic cloth fibers, felt, and sponge. Bibulous filter paper is commonly used and is preferred.

The liquids that are useful as solvents for iron protoporphyrins and which are preferably used herein typically have an intermediate to high capacity to dissolve iron protoporphyrins at a pH in the range of about 5.0 to 10.0. In the present instance such capacity was determined by mixing 25 mg crystalline hemin with 1 ml of solvent at ambient temperature, and measuring the amount of hemin remaining undissolved. Liquids evaluated by this procedure that exhibited a high capacity for dissolving hemin included aprotic amides, sulfoxides, sulfones, pyridine and mixtures of certain amines and other organic solvents.

The amides that were found to be acceptable iron protoporphyrin solvents are of the formula

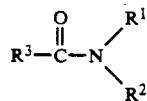

wherein $R^1$, $R^2$, and $R^3$ are the same or different and represent hydrogen, lower alkyl, phenyl or benzyl, with the provisos that both of $R^1$ and $R^2$ are not hydrogen and $R^3$ may be linked with $R^1$ or $R^2$ to form a 5- or 6-membered heterocycle. The term "lower" as used to modify "alkyl" denotes moieties of 1 to 6 carbon atoms. Examples of such moieties are methyl, ethyl, isopropyl, butyl, and hexyl. Dimethyl formamide, tetramethyl urea and 1-methyl-2-pyrrolidinone are preferred solvents of this class.

Sulfoxides and sulfones that were found to be acceptable iron protoporphyrin solvents are of the formula

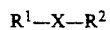

wherein X is

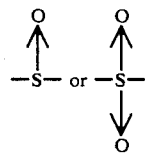

and $R^1$ and $R^2$ are the same or different and are lower alkyl, phenyl, benzyl, or, when X is

$R^1$ and $R^2$ may be linked to form a 5 or 6 membered heterocycle (e.g., tetramethylene sulfoxide, pentamethylene sulfoxide).

The mixtures of neutralized amines and organic solvents that were found to be acceptable iron protoporphyrin solvents include: ethanolamine with glycerol, tetrahydrofurfuryl alcohol, 2-methoxy ethanol, methyl ethyl ketone, tetramethyl urea, sulfolane (tetramethylene sulfone), or butyrolactone; 2-(diethylamino)ethylamine with methyl ethyl ketone, acetonitrile, sulfolane, butyrolactone, tetrafurfuryl alcohol, 2-methoxy ethanol, or methanol and diethanolamine with methyl ethyl ketone, acetonitrile, sulfolane, butyrolactone, or tetrahydrofurfuryl alcohol. Other mixtures of neutralized amines and organic solvents that are suitable solvents for iron protoporphyrin may be determined empirically as described herein. The mixtures are preferably mixed at volume ratios of approximately 1:1 based on 1M aqueous neutralized amine.

The iron protoporphyrin solvent is also preferably one that wets the test matrix so that it is capable of transporting (chromatographing) dissolved iron protoporphyrin away from the specimen so that the color change, if any, is more easily seen and not obscured by the specimen.

A particularly preferred solvent for use herein is a mixture of tetramethyl urea and ethanolamine or dimethylamine, the mixture containing about 50–90 vol. % tetramethyl urea and, correspondingly, about 10–50% ethanol mine or dimethylamine. An optimal formulation contains about 70 vol % tetramethyl urea and about 30 vol. % ethanolamine or dimethylamine.

Hydrogen peroxide or organic hydroperoxides such as cumene hydroperoxide, t-butyl hydroperoxide, diisopropylbenzene hydroperoxide, and 2,5-dimethylhexane hydroperoxide may be used in the developer or complete reagent. It is preferred to use an organic hydroperoxide since organic hydroperoxides are less likely to (a) produce false positive results in FOBT in which vegetable peroxidases are present in the fecal specimen and (b) destroy the peroxidase activity of the hemoprotein. The concentration of hydroperoxide in the developer/complete reagent will usually be in the range of 0.05 to 10% by volume, more usually 0.5 to 5% by volume.

The modulating compounds which are used in conjunction with the present invention are typically included in the solution which contains the solvent for iron protoporphyrins. These modulating compounds are antimalarial drugs that include both accelerators, i.e., compounds which enhance the rate of the colorimetric reaction, and inhibitors, i.e., compounds which slow down that reaction.

The accelerators used herein are chloroquine (I) and quinacrine (II):

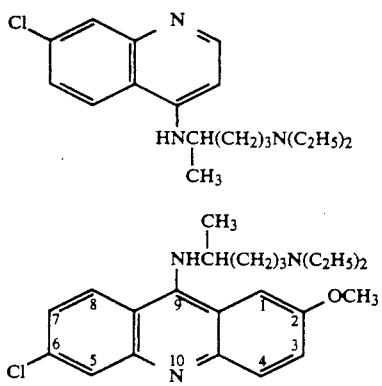

These compounds may be used as shown, in Lewis base form, or as salts, e.g., halides such as chloroquine or quinacrine hydrochloride. These compounds permit very rapid detection of peroxidatively active substances, e.g., fecal blood. The accelerators may be included in the solution containing the solvent for iron protoporphyrins in an amount ranging from about 0.1% to about 5.0%, optimally about 1.5%.

It is in fact quite unexpected that the aforementioned compounds act as accelerators of peroxidase activity, as it has been well-established in the art that chloroquine and quinacrine both inhibit enzyme activity. See, e.g.: Fraser and Kermack, *Br. J. Pharmac. Chemother.* 12:16-23 (1957)(inhibition of hexokinase by chloroquine); Gerhlach, *Klin. Wschr.* 36:376-78 (1958)(inhibition of glutamic dehydrogenase by chloroquine diphosphate); Vanderjagt et al., *Molecular and Biochem. Parasit.* 10:45-54 (1984)(inhibition of an aminopeptidase by chloroquine and quinacrine); and Shute et al., *Biochemical Pharmacology* 34:2471-75 (1985)(inhibition of phosphatidylinositol phosphodiesterase by chloroquine). Furthermore, it should be noted that while all of the antimalarial drugs disclosed as modulating compounds herein contain the quinoline nucleus, quinoline itself has no significant effect on catalysis. As established in the art and as demonstrated in the experimental section below, catalytic enhancement is not a general property of quinoline-based antimalarial drugs. Of the drugs tested by the inventor herein, only chloroquine and quinacrine effectively enhance the catalytic activity of hemin and hemoglobin.

These accelerator compounds in tests for detecting peroxidatively active substances, particularly FOBT, provides a significant advantage over the art. In many FOBT, color formation can be quite slow, i.e., two to five minutes may be needed for full color development in some specimens. Further, color development is particularly slow in smears that contain mainly iron protoporphyrin rather than hemoglobin itself. This type of specimen can be anticipated whenever a patient has a bleeding upper GI lesion or collects test specimens for three days and mails or delivers the specimen to his physician. This limitation produces a very high incidence of false negative test results with current FOBT product. Inclusion of the accelerator compounds disclosed herein, however, will produce a reliable, clear positive test result under the aforementioned circumstances. That is, an FOBT formulated with these accelerators will detect blood released anywhere in the G.I. tract with an intense, stable blue color in less than two minutes.

Turning now to the class of modulating compounds which are "inhibitors", it should first of all be pointed out that a key element in developing tests for detecting peroxidatively active substances is the ability to regulate test sensitivity. This is particularly true when the test relies on guaiac as the chromogen and when the test is intended for use with human or animal fecal specimens. Unlike many other chromogens which are pure compounds, guaiac is a crude plant extract containing numerous compounds. The actual chromogen in the crude guaiac extract represents a very small and variable percent of the total extract. As a result, it is difficult to modulate test sensitivities reliably by simply altering the concentration of crude guaiac in a reagent formulation.

In addition, fecal specimens, even from a single species, vary enormously in water content, fiber content, food residues, endogenous heme content, and the like. The problem is compounded when specimens from various species are to be tested. A test sensitivity appropriate for one species may be completely inappropriate for other species. Tests for occult blood other than that present in feces also have inherently different sensitivity requirements.

Ordinarily, FOBT sensitivity is regulated by empirically changing the concentration of the chromogen or oxidant. Unfortunately, decreasing the chromogen or oxidant concentration also decreases color intensity from a positive test and increases the rate of color fading. As a result, the test sensitivity defined by a given chromogen concentration can produce a color reaction that is unacceptably faint. Ideally, then, it should be possible to modify test sensitivity by a mechanism other than changing chromogen concentration. To date, however, no such mechanism has been proposed. The present invention addresses this need in the art by the inclusion of various inhibitory compounds in FOBT and other tests for detecting peroxidatively active materials.

The compounds which the inventor herein has found to be inhibitory of the colorimetric reaction described in this application are quinidine (III), quinine (IV) and primaquine (V):

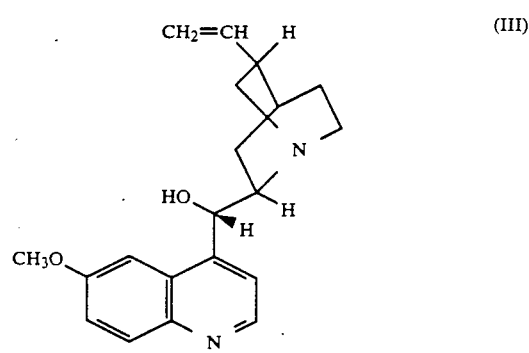

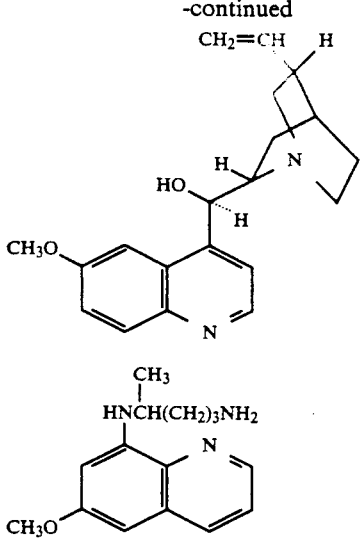

Since the above-represented compounds may be seen to be structurally quite similar to the accelerators described earlier, it is in fact quite surprising that the above-represented compounds act as inhibitors in the FOBT described herein and analogous tests. U.S. Pat. No. 3,917,452 to Rittersdorf in fact supports that quinine is a stimulator of peroxidative activity; see also West German Patent No. 1,242,905, cited therein, and U.S. Pat. Nos. 3,290,117, 3,975,161 and 4,148,611 which also disclose the use of quinine as an accelerator of peroxidative activity. In view of these disclosures, it is indeed surprising to find that quinine (and related compounds quinidine and primaquine) are potent inhibitors in the FOBT described herein.

Use of these inhibitors alone or in conjunction with the aforementioned accelerators enables careful control of test sensitivity at single defined concentration of chromogen, e.g., of guaiac or a guaiac/ABTS mixture.

After selection of a particular chromogen concentration, the relative amounts of accelerators and/or inhibitors included in the developer or reagent composition are varied to optimize test sensitivity and specificity. The amount of each, if present, is in the range of from about 0.01% to about 10.0%; this range corresponds to a typical chromogen concentration of between about 0.1% and 6.0%. At an optimal chromogen concentration in the range of from about 0.1 to about 1.0%, a particularly preferred composition includes about 1.5% accelerator and about 1.5% inhibitor. (Note: all "%" values are given as weight per volume of solution, i.e., 1 g/100 ml = 1%.)

As noted above, a good FOBT should have both high sensitivity (low incidence of false negative test results) and high specificity (low incidence of false positive test results). Numerous publications clearly show that current FOBT have a false positive test incidence of 5 to 10 percent or higher. These result in an increased clinical burden, with a significant impact on cost effectiveness for colorectal cancer screening, where the incidence of false positive tests is highest. Moreover, the follow-up diagnostic procedures (x-ray, colonoscopy, endoscopy, etc.) are expensive, uncomfortable, time-consuming, and have a significant rate of morbidity and mortality.

One major cause of false positive FOBT results is the elevated concentrations of fecal ferriprotoporphyrins resulting from ingestion of meat in the diet. If meat is ingested during the few days needed to complete an FOBT evaluation, the likelihood of a false positive FOBT result increases quite markedly due to the additional fecal ferriprotoporphyrins that are present. Patients are thus instructed to refrain from meat ingestion during these few days needed to complete an FOBT evaluation, but compliance is often poor. Moreover, if the FOBT is to be used in a veterinary setting with carnivores, avoidance of meat ingestion is impractical.

The present invention provides a solution to this problem. The inhibitors described above may be used to eliminate fecal occult blood test interference from dietary meat. Addition of quinine, primaquine or quinidine to fecal specimens prior to carrying out the colorimetric test for peroxidative activity significantly raises the threshold level of hemin detection. That is, by adding about 50 µl of a 0.1-10% quinine, primaquine or quinidine solution to a fecal specimen, it is possible to produce a positive test only above a specific threshold concentration of hemin, typically 0.03 mg hemin/g feces. In the absence of inhibitors, hemin levels as low as 0.007 mg/g can be detected. Thus, in an additional embodiment of the invention, a method is provided for carrying out an FOBT while minimizing interference from dietary meat ingestion.

Hemoprotein solubilizing agents that may be optionally included in the solution or test matrix include detergents and water-soluble polymers. Detergents that have suitable hydrophilic-hydrophobic balance to solubilize hemoproteins are preferred. Such detergents include the TRITON ® detergents (polyoxyethylene alkylphenols), detergents from the series alkyltrimethylammonium bromides, like cetyl alkyltrimethylammonium bromide (CTAB) or p-toluene sulfonic acid salts of alkyltrimethylammonium bromide detergents, and $C_{10}$ to $C_{14}$ alkali metal salts of fatty acids or alkali metal alkyl sulfates. Examples of suitable detergents are sodium dodecyl sulfate (SDS), sodium dodecyl sulfonate, sodium decyl sulfate, sodium tetradecyl sulfate, sodium tridecyl sulfonate, sodium myristate, sodium caprate, sodium dodecyl N-sarcosinate, and sodium tetradecyl N-sacrosinate. The water-soluble polymers that may be used to solubilize hemoproteins include poly(ethylene oxide), poly(vinyl alcohol), poly(vinyl pyrrolidone), poly(vinyl pyridine), and poly(styrene sulfonate). These solubilizing agents not only solubilize hemoproteins, but are believed to convert perioxidatively inactive hemoprotein dimers or aggregates into peroxidatively active monomeric species.

Nitrogenous ligands that stabilize iron protoporphyrins and enhance their peroxidative activity may also be incorporated in the complete reagent or test matrix. Examples of such ligands are pyridine, histidine, caffeine, imidazole, and imidazole derivatives.

Other additives such as vegetable peroxidase inhibitors and iron chelators (e.g., ethylenediamine tetraacetic acid-N, N, N', N'-diamino cyclohexane tetraacetic acid, citric acid, tartaric acid, nitrilotriacetic acid, diethylenetriamine-pentaacetic acid, N,N'-bishydroxyethyl glycine, ethyleneglycol bis(2aminoethylether)-tetraacetic acid, N-hydroxyethyl ethylenediaminetetraacetic acid) may be incorporated into the test matrix to further reduce the likelihood of false test results. Buffers are added to maintain a suitable pH range for oxidizing the leuco dye. The particular buffer (pH range) will depend on the leuco dye that is used. The pH will usually be between about 3 and about 9. By way of example, guaiac oxidation is buffered at pH 6-7.5 (phosphate buffer), 3,3',5,5'-tetramethylbenzidine oxidation is buffered at a pH of about 4 (acetate buffer), and ABTS is buffered at a pH of about 9–9.5 (glycine buffer). For the chromogen mixture of the invention the pH should be in the range of 5 to 10.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Tests were carried out to ascertain the effect of chloroquine on the rate and extent of color formation in the hemin-catalyzed oxidation of guaiac. The following reagents were used: (1) a solution of about 10% guaiac in a solvent mixture consisting of approximately 70 mol. %, tetramethyl urea (TMU) and approximately 30 vol. % 1M ethanolamine (EA), pH 7.0; (2) 4% chloroquine in a TMU/EA solvent mixture (60:40 vol/vol); (3) 5% cumene hydroperoxide; and (4) hemin suspension, 0.16 mg/ml in distilled water.

Test procedure: Samples were prepared by adding twenty microliters of hemin suspension to 3.0 ml of a TMU/EA (60:40 vol/vol) solvent mixture containing 5% guaiac, 5% cumene hydroperoxide, and chloroquine at the various concentrations indicated in Table 1. The final hemin concentration in each case was 1.07 micrograms/ml. Optical scans of the system were made between 400 and 800 nm at 30 second intervals. The peak optical densities at 610 nm ($OD_{610}$) are set forth in Table 1.

TABLE 1

| Chloroquine Conc. | Optical Density at 610 nm | | | | |
|---|---|---|---|---|---|
| | 30 sec | 60 sec | 90 sec | 120 sec | 150 sec |
| 0.00 | 0.048 | 0.096 | 0.096 | 0.144 | 0.144 |
| 0.01 | 0.048 | 0.144 | 0.240 | 0.288 | 0.336 |
| 0.1 | 0.144 | 0.432 | 0.624 | 0.768 | 0.864 |
| 0.5 | 0.336 | 0.672 | 0.962 | 1.104 | 1.104 |
| 1.0 | 1.776 | 2.304 | >2.5 | >2.5 | >2.5 |
| 2.0 | 1.344 | 2.30 | 2.30 | 2.30 | 2.30 |

The color observed at 610 nm results from the hemin-catalyzed oxidation of guaiac using cumene hydroperoxide as oxidant. As may be seen in Table 1, when chloroquine is added to such a system, both the rate and the intensity of color formed are substantially enhanced. The enhancing effect appears to be roughly proportional to the chloroquine concentration. A minor enhancement is seen at 0.01% chloroquine and enhancement appears to reach a maximum at about 1–2% chloroquine. In sum, chloroquine substantially enhances test sensitivity.

EXAMPLE 2

The tests carried out in Example 1 were re-run using hemoglobin, horse radish peroxidase (HRP) and ferric chloride as catalysts. The following reagents were used: (1) a solvent mixture of tetramethyl urea and 1M ethanolamine, 60:40 vol/vol pH 7.0 ("TMU/EA solvent"); (2) 10% guaiac in TMU/EA solvent; (3) 4% chloroquine in TMU/EA solvent; (4) cumene hydroperoxide; (5) hemin suspension, 0.16 mg/ml in distilled water (final reaction concentration, 3.2 µg/ml); (6) hemoglobin, 3 mg/ml in distilled water (final reaction concentration, 60 micrograms/ml); (7) horse radish peroxidase, 300 U/ml in distilled water (final reaction concentration, 6 U/ml); and (8) ferric chloride, 100 mM (final reaction concentration, 324 µg/ml).

Test procedure: Samples were prepared by adding twenty microliters of catalyst solution (i.e., hemin, hemoglobin, HRP, or ferric chloride) to 1.0 ml of a TMU/EA solution containing 5% guaiac, 5% cumene hydroperoxide, and chloroquine at the concentrations indicated in Tables 2a through 2d. Initial rate of increase in optical density ($V_{init}$, defined as the change in optical density at 610 nm during the first thirty seconds of reaction) was noted, along with the maximum optical density at 610 nm over a 300 second reaction interval ($OD_{max}$), and, in the case of HRP, over a 60 second reaction interval ($OD_{60}$).

TABLE 2a

| Catalyst = Hemin | | | | |
|---|---|---|---|---|
| Final Chloroquine Concentration (Percent) | | | | |
| Parameter | 0.0 | 0.5 | 1.0 | 2.0 |
| V Init | 0.114 | 0.087 | 0.470 | 0.874 |
| OD max | 0.448 | 0.462 | 1.063 | 1.426 |

TABLE 2b

| Catalyst = Hemoglobin | | | | |
|---|---|---|---|---|
| Final Chloroquine Concentration (Percent) | | | | |
| Parameter | 0.0 | 0.5 | 1.0 | 2.0 |
| V Init | 0.223 | 0.562 | 1.018 | 1.461 |
| OD max | 0.607 | 1.114 | 1.642 | 2.079 |

TABLE 2c

| Catalyst = Horseradish Peroxidase | | | | |
|---|---|---|---|---|
| Final Chloroquine Concentration (Percent) | | | | |
| Parameter | 0.0 | 0.5 | 1.0 | 2.0 |
| V Init | 1.777 | 1.646 | .656 | 1.033 |
| OD 60 Sec | 1.373 | .873 | .361 | .541 |

TABLE 2d

| Catalyst = Ferric Chloride | | | | |
|---|---|---|---|---|
| Final Chloroquine Concentration (Percent) | | | | |
| Parameter | 0.0 | 0.5 | 1.0 | 2.0 |
| V Init | 2.064 | 1.744 | 0.099 | 0.000 |
| OD max | 2.062 | 1.749 | 0.099 | 0.000 |

It may be concluded from these tests that chloroquine enhances the rate of color formation and maximum color intensity regardless of whether hemin or hemoglobin is used as the catalyst. This is an important advantage, as fecal occult blood may consist of hemin, hemoglobin, or a mixture of both, and it is therefore highly desirable to be able to detect both entities regardless of their relative amounts in feces.

Even more surprisingly, chloroquine inhibits catalysis by both HRP and ferric chloride. It is well known that plant peroxidases are potentially a significant cause of false positive test results. Thus, inhibition of HRP by chloroquine indicates that chloroquine can generally inhibit plant peroxidase activity, eliminating a key cause of false positives. Similarly, iron salts are known to cause false positive test results. Such salts are frequently consumed by patients either as prescribed or as over-the-counter mineral supplements. Also, fecal specimens retrieved from toilet bowl water may contain iron salts are a result of rust formation in the plumbing system.

Consequently, the fact that chloroquine inhibits catalysis by ferric chloride is yet another indication of how the compound can significantly reduce the incidence of false positives and thus enhance test specificity.

EXAMPLE 3

The effect of a variety of antimalarial drugs on hemin-750 and hemoglobin-catalyzed guaiac oxidation was studied using a procedure similar to that of the proceeding examples. The following reagents were used: (1) hemin, 0.03 mg/ml in distilled water (prepared by dissolving hemin in DMSO and adding the concentrated DMSO solution to water; final reaction concentration 0.0006 mg/ml); (2) TMU, diluted to 70 percent with 1M ethanolamine, pH 7.0; (3) hemoglobin, 0.6 mg/ml in water (final reaction concentration, 0.012 mg/ml); and (4) chromogen solution containing 0.5% guaiac/ 1.0% ABTS in chromogen solution containing 0.5% guaiac/ 1.0% ABTS in TMU/EA (70:30 vol/vol) and 5% cumene hydroperoxide.

Test procedure: Samples were prepared by adding twenty microliter aliquots of hemin suspension or hemoglobin solution to the chromogen solution containing ether, water or the drug indicated (final concentration 1.5%), and the optical density at 610 nm was monitored for 90 seconds.

Results are set forth in Tables 3 and 4.

TABLE 3

| | Optical Density at 610 nm - HEMIN CATALYSIS | | | | | |
|---|---|---|---|---|---|---|
| Time (sec) | None | Chloroquine | Quinacrine | Quinoline | Primaquine | Quinine |
| 0 | 0.000 | 0.000 | 0.000 | 0.000 | 0.000 | 0.000 |
| 30 | 0.360 | 1.475 | 1.059 | 0.423 | 0.014 | 0.019 |
| 60 | 0.770 | 1.483 | 1.670 | 0.945 | 0.030 | 0.040 |
| 90 | 0.987 | 1.246 | 1.789 | 1.168 | 0.048 | 0.060 |

TABLE 4

| | Optical Density at 610 nm - HEMOGLOBIN CATALYSIS | | | | | |
|---|---|---|---|---|---|---|
| Time (sec) | None | Chloroquine | Quinacrine | Quinoline | Primaquine | Quinine |
| 0 | 0.000 | 0.000 | 0.000 | 0.000 | 0.000 | 0.000 |
| 30 | 0.282 | 1.474 | 0.873 | 0.416 | 0.021 | 0.029 |
| 60 | 0.564 | 1.431 | 1.339 | 0.743 | 0.039 | 0.058 |
| 90 | 0.689 | 1.159 | 1.450 | 0.884 | 0.057 | 0.080 |

All of the antimalarial drugs tested contain the quinoline nucleus; nonetheless, quinoline itself had no significant effect on catalysis. Further, it may be concluded that catalytic enhancement is not a general property of quinoline-based antimalarial drugs. Of the drugs tested, only chloroquine and quinacrine effectively enhanced the catalytic activity of hemin and hemoglobin. Both the rates and intensity of color formed were enhanced.

In contrast to chloroquine and quinacrine, structurally similar compounds quinine, primaquine and quinidine strongly inhibit catalysis by both hemin and hemoglobin.

EXAMPLE 4

The effect of quinine and quinidine on the hemin- and hemoglobin-catalyzed oxidation of guaiac was studied as follows.

A. Quinine studies.

1. The following reagents were prepared and used in this section: (1) hemin suspension (HM), 0.03 mg/ml in distilled water (final reaction concentration, 0.0006 mg/ml); (2) hemoglobin solution (HB), 0.6 mg/ml in distilled water (final reaction concentration, 0.012 mg/ml); (3) Reagent I (chromogen solution), 0.5% guaiac, 1.5% chloroquine, 5.0% cumene hydroperoxide, 1.0% ABTS in TMU/EA (70:30 vol/vol), pH 7.0; (4) Reagent II: Reagent I plus 0.1% quinine; (5) Reagent III: Reagent I plus 0.5% quinine; (6) Reagent IV: Reagent I plus 1.0% quinine; and (7) Reagent V: Reagent I plus 2.0% quinine.

Test procedure: Samples were prepared by adding twenty microliters of hemin suspension or hemoglobin solution to 1.0 ml of the reagent indicated. The optical density of 610 nm was monitored for 90 seconds, and the optical densities at 30 second intervals are given in Table 5.

TABLE 5

| Time | Reagent I | | Reagent II | | Reagent III | | Reagent IV | | Reagent V | |
|---|---|---|---|---|---|---|---|---|---|---|
| (Sec) | HB | HM | HB | HM | HB | HM | HB | HM | HB | HM |
| 0 | 0.000 | 0.000 | 0.000 | 0.000 | 0.000 | 0.000 | 0.000 | 0.000 | 0.000 | 0.000 |
| 30 | 0.603 | 1.646 | 0.378 | 1.013 | 0.127 | 0.305 | 0.080 | 0.158 | 0.040 | 0.083 |
| 60 | 0.693 | 2.006 | 0.541 | 1.558 | 0.226 | 0.615 | 0.146 | 0.350 | 0.070 | 0.173 |
| 90 | 0.631 | 1.936 | 0.554 | 1.694 | 0.292 | 0.837 | 0.192 | 0.502 | 0.091 | 0.224 |

LEGEND:
HB = Hemoglobin
HM = Hemin

2. The following reagents were prepared and used in this section: (1) hemin suspension, 0.03 mg/ml in distilled water (prepared by dissolving hemin in DMSO and adding the concentrated DMSO solution to distilled water, final reaction concentration 0.0006 mg/ml); and (2) chromogen solution, 1.5% guaiac, 1% ABTS, 1.8% 1,2-diaminocyclohexane-n,n,n',n'-tetraacetic acid (DACHTAA), 5% cumene hydroperoxide, 1.5% chloroquine, and quinine as indicated in Table 6.

Test procedure: Twenty microliters of hemin suspension was added to 1 ml of the chromogen solution. The optical density at 610 nm was monitored for 300 seconds; results are set forth in Table 6.

TABLE 6

| Quinine Conc. (%) | Optical Density (60 sec) | Maximum Rate | Maximum Optical Density |
| --- | --- | --- | --- |
| 0.0 | 0.910 | 0.538 | 1.212 |
| 0.1 | 0.611 | 0.340 | 1.078 |
| 0.25 | 0.367 | 0.191 | 0.869 |
| 0.5 | 0.222 | 0.115 | 0.754 |
| 1.0 | 0.113 | 0.062 | 0.391 |

As may be concluded from Sections A.1 and A.2 of this example, quinine can inhibit hemin and hemoglobin catalysis in the presence of the accelerator chloroquine. Even at a final concentration of only 0.1 percent, as illustrated in Tables 5 and 6, quinine significantly inhibits catalysis by both hemin and hemoglobin in the presence of 1.5% chloroquine.

B. Quinidine studies

1. A procedure similar to that followed in part A.1 of this example was used to study the effect of quinidine on the hemin-catalyzed oxidation of guaiac in the presence of chloroquine.

Reagents used: (1) hemin suspension, 0.3 mg/ml in distilled water (prepared as above using DMSO); (2) Reagent I (chromogen solution), 2% quinidine, 0.5% guaiac, 1% ABTS, 1.5% chloroquine, 5% cumene hydroperoxide, in TMU/EA (70:30 vol/vol, ethanolamine at 1M). pH 7.0; (3) Reagent II: same as Reagent I, except containing 1.0% quinidine; (4) Reagent III: same as Reagent I, except containing 0.5% quinidine; (5) Reagent IV: same as Reagent I, except containing 0.1% quinidine; and (6) Reagent V: same as Reagent I, except containing no quinidine (CONTROL).

Test procedure: Samples were prepared by adding twenty microliters of the hemin suspension to 1.0 ml of Reagents I, II, III, IV or V. The optical densities of the samples at 610 nm were monitored for 150 seconds and are tabulated in Table 7.

TABLE 7

| | Optical Density | | | | |
| --- | --- | --- | --- | --- | --- |
| Time (Sec) | Reagent I 2.0% quinidine | Reagent II 1.0% quinidine | Reagent III 0.5% quinidine | Reagent IV 0.1% quinidine | Reagent V 0.0% quinidine |
| 0 | 0.000 | 0.000 | 0.000 | 0.000 | 0.000 |
| 30 | 0.026 | 0.029 | 0.036 | 0.140 | 0.713 |
| 60 | 0.026 | 0.043 | 0.071 | 0.316 | 1.250 |
| 90 | 0.030 | 0.057 | 0.105 | 0.470 | 1.465 |
| 120 | 0.034 | 0.071 | 0.138 | 0.067 | 1.531 |
| 150 | 0.040 | 0.085 | 0.167 | 0.726 | 1.536 |

2. A procedure similar to that outlined in Section A.2. of this example was followed to ascertain the effect of quinidine on the rate of hemin-catalyzed guaiac oxidation. The reagents and test procedure were identical to that used in Section B.1, and results are set forth in Table 8:

TABLE 8

| Qunidine Conc. | Optical Density 60 sec | Maximum Optical Density | Maximum Change Rate |
| --- | --- | --- | --- |
| 2.0% | 0.026 | 0.056 | 0.026 |
| 1.0% | 0.043 | 0.141 | 0.028 |
| 0.5% | 0.071 | 0.286 | 0.035 |
| 0.1% | 0.316 | 1.072 | 0.175 |
| 0.0% | 1.250 | 1.536 | 0.713 |

As Tables 7 and 8 illustrate, quinidine, an epimer of quinine, is even more effective than quinine in inhibiting hemin catalysis. Significant inhibition of hemin catalysis is seen at 0.1% quinidine, and inhibition is virtually complete at 2.0% quinidine.

EXAMPLE 5

The following studies were done to vary test sensitivity over a broad range using the antimalarial drugs quinine and quinidine.

A. Quinine. The following reagents were used: (1) hemin suspension, 0.03 mg/ml in distilled water (prepared using DMSO as above); (2) chromogen solution without quinine ("−QUINE" in Table 9), containing 1.5% guaiac, 2.0% DACHTAA, 1% ABTS, 5% CHP in TMU/ 30% diethylamine, 1M, and chloroquine as indicated in Table 9, pH approximately 6.5; and (3) chromogen solution with quinine ("+QUINE" in Table 9), same as the preceding solution, but with 0.5% quinine added.

The test procedure was as follows. Twenty microliters of hemin suspension were added to the chromogen solutions. The optical density at 610 nm was monitored for 300 seconds

TABLE 9

| Chloroquine (Conc.) | Optical Density (60 sec) | | Maximum Rate Change | | Maximum Optical Density | |
| --- | --- | --- | --- | --- | --- | --- |
| % | +Quine | −Quine | +Quine | −Quine | +Quine | −Quine |
| 0.00 | 0.024 | 0.048 | 0.022 | 0.032 | 0.146 | 0.242 |
| 0.25 | 0.071 | 0.113 | 0.055 | 0.059 | 0.286 | 0.453 |
| 0.50 | 0.102 | 0.257 | 0.055 | 0.031 | 0.452 | 0.623 |
| 0.75 | 0.122 | 0.406 | 0.058 | 0.216 | 0.503 | 0.732 |
| 1.00 | 0.199 | 0.579 | 0.060 | 0.324 | 0.522 | 0.956 |

B. Quinidine. The following reagents were used: (1) hemin suspension, 0.03 mg/ml in distilled water, prepared using DMSO as above; (2) Reagent I: 1.5% guaiac, 1.5% chloroquine, 1.0% ABTS, 1.8% DACHTAA, 5% cumene hydroperoxide, in a solution of tetramethyl urea and 1M diethylamine (70:30 vol/vol; "TMU/DEA"), pH 7.0; (3) Reagent II: 75 vol. % Reagent I in TMU/DEA; (4) Reagent III: 50 vol. % Reagent I in TMU/DEA; (5) Reagent IV: 40 vol. % Reagent I in TMU/DEA; and (6) Reagent V: 30 vol. % of Reagent I in TMU/DEA. Twenty microliters of hemin suspension was added to 1.0 ml of the reagent indicated in Table 10, and the optical density at 610 nm was monitored for 300 seconds. Results are tabulated below.

TABLE 10

| Reagent | Optical Density (60 sec) | Maximum Optical Density | Maximum Rate |
| --- | --- | --- | --- |
| 100% | 0.927 | 1.240 | 0.528 |
| 75% | 0.702 | 1.103 | 0.343 |
| 50% | 0.514 | 0.951 | 0.266 |
| 40% | 0.340 | 0.734 | 0.174 |

TABLE 10-continued

| Reagent | Optical Density (60 sec) | Maximum Optical Density | Maximum Rate |
|---|---|---|---|
| 30% | 0.110 | 0.575 | 0.110 |

As may be concluded from the studies summarized in this example, including inhibitory antimalarial drugs in an FOBT reagent containing chloroquine enables one to vary test sensitivity over a broad range. In Tables 9 and 10, it should be noted that the rate of color formation, the intensity of color at 60 seconds, and the maximum color obtainable can all be significantly modified by the use of appropriate levels of stimulatory and inhibitory antimalarials.

EXAMPLE 6

The effect of quinine, quinidine and primaquine on test sensitivity was evaluated using normal canine fecal specimens spiked with decreasing quantities of hemin.

A. Quinine. The following reagents were used: (1) hemin suspensions as indicated below; (2) 1.5% guaiac, 1.5% chloroquine, 1% ABTS, 1.8% DACHTAA, 5% CHP in 70% TMU/30% Diethylamine 1M, pH 7.0; (3) Reagent I: 2% quinine in 70% TMU/Diethylamine 1M, pH 7.0; (4) Reagent II: Same as Reagent I, except 1% quinine; (5) Reagent III: Same as Reagent I, except 0.5% quinine; (6) Reagent IV: Same as Reagent I, except 0.2% quinine; (7) Reagent V: Same as Reagent I, except 0.1% quinine; (8) Reagent VI: Same as Reagent I, except 0.05% quinine; (9) Reagent VII: Same as Reagent I, except 0.00% quinine; and (10) Reagent VIII: Control - No addition.

Test procedure: Multiple 1-2 g aliquots were weighed from a well-mixed canine fecal specimen which had produced a negative test result on both the Hemoccult ® and prototype FOBT. Aqueous suspensions of hemin were prepared at concentrations 3-fold higher than the desired concentrations in feces. The indicated concentration (mg compound/g feces) was prepared by adding a mass of aqueous hemin equivalent to 0.5 times the mass of the given sample. Each spiked sample was mixed until uniform consistency was obtained and fecal smears were made on Whatman #1 filter paper and allowed to dry at room temperature. Twenty microliters of the reagent indicated was added to each fecal smear. The paper was dried at 50° C. for 30 minutes. Twenty microliters of the 1.5% guaiac Reagent (2) was added to each spot. The color intensity and migration were determined at 1, 2, and 5 minutes. Results are set forth in Table 11. (Legend: Color Intensity: 0=no perceptible blue color; +1=barely perceptible blue color; +10=intense, solid blue color; intermediate ratings=blue color of intermediate intensity. Color Migration: 0=no color migration, color is formed, but fails to move from the catalyst spot; 10=complete movement of color from the specimen to the solvent front; intermediate ratings=movement of color between solvent front and the catalyst spot.

TABLE 11

| | Test Appearance at 1 Minute Quinine Concentration | | | | | | | | | | | | | |
|---|---|---|---|---|---|---|---|---|---|---|---|---|---|---|
| Fecal Hemin | Reagent I 2.0% | | Reagent II 1.0% | | Reagent III 0.5% | | Reagent IV 0.2% | | Reagent V 0.1% | | Reagent VI .05% | | Reagent VIII Control | |
| mg/gram | MIG | INT | MIG | INT | MIG | INT | MIG | INT | MIG | INT | MIG | INT | MIG | INT |
| 0.12 | 5 | 7 | 5 | 7 | 5 | 7 | 5 | 7 | 5 | 7 | 5 | 7 | 8 | 7 |
| 0.06 | 2 | 3 | 3 | 2 | 3 | 2 | 4 | 2 | 4 | 2 | 4 | 3 | 7 | 3 |
| 0.03 | 2 | 1 | 3 | 1 | 3 | 1 | 3 | 1 | 3 | 2 | 3 | 2 | 5 | 2 |
| 0.015 | 0 | 0 | 0 | 0 | 0 | 0 | 0 | 0 | 0 | 0 | 2 | .5 | 4 | 1 |
| 0.007 | 0 | 0 | 0 | 0 | 0 | 0 | 0 | 0 | 0 | 0 | 0 | 0 | 3 | 0.5 |

"MIG": Color migration. 0 = no color formation; color is formed, but fails to move from the catalyst spot; 10 = complete movement of color from the specimen to the solvent front; intermediate ratings = movement of color between solvent front and the catalyst spot.
"INT": Color intensity. 0 = no perceptible blue color; +1 = barely perceptible blue color; +10 = intense, solid, blue color; intermediate ratings = blue color of intermediate intensity.

In this section of the example, spiked fecal specimens were tested with a prototype FOBT reagent in the presence and absence of added quinine. In the absence of quinine, a positive test result was seen at hemin concentrations as low as 0.007 mg hemin/g feces. The addition of 0.05% quinine to the fecal specimens prior to addition of the developing FOBT reagent prevented blue color formation at 0.007 mg hemin/g feces.

Addition of a 0.1% quinine solution to the specimens prevented detection of hemin at a concentration of 0.15 mg/g feces. As the concentration of hemin was increased, the addition of quinine no longer eliminated color response even at concentrations of 2% quinine. Thus, by adding appropriate concentrations of quinine to fecal smears, it is possible to produce a positive test only above a specific threshold concentration of hemin.

B. Primaquine. The same reagents and procedure as in part A of this example were used, except that primaquine was substituted for quinine. Results are shown in Table 12.

TABLE 12

| | Test Appearance at 1 Minute Primaquinine Concentration | | | | | | | | | | | | | |
|---|---|---|---|---|---|---|---|---|---|---|---|---|---|---|
| Hemin | Reagent I 2.0% | | Reagent II 1.0% | | Reagent III 0.5% | | Reagnet IV 0.2% | | Reagent V 0.1% | | Reagent VI .05% | | Reagent VIII Control | |
| mg/gram | MIG | INT | MIG | INT | MIG | INT | MIG | INT | MIG | INT | MIG | INT | MIG | INT |
| 0.24 | 8 | 3 | 8 | 3 | 10 | 3 | 10 | 4 | 10 | 4 | 10 | 5 | 10 | 10 |
| 0.12 | 3 | 1 | 3 | 1 | 3 | 1 | 3 | 3 | 4 | 3 | 5 | 5 | 10 | 10 |
| 0.06 | 5 | 1 | 8 | 1 | 3 | 2 | 5 | 1 | 5 | 2 | 5 | 2 | 9 | 7 |
| 0.03 | 5 | 1 | 5 | 1 | 5 | 0.5 | 5 | 1 | 4 | 1 | 4 | 1 | 8 | 3 |
| 0.015 | .5 | .5 | 0 | 0 | 0 | 0 | 0 | 0 | 0 | 0 | 0 | 0 | 7 | 2 |

TABLE 12-continued

| | Test Appearance at 1 Minute | | | | | | | | | | | | | |
|---|---|---|---|---|---|---|---|---|---|---|---|---|---|---|
| | Primaquinine Concentration | | | | | | | | | | | | | |
| | Reagent I 2.0% | | Reagent II 1.0% | | Reagent III 0.5% | | Reagnet IV 0.2% | | Reagent V 0.1% | | Reagent VI .05% | | Reagent VIII Control | |
| Hemin mg/gram | MIG | INT | MIG | INT | MIG | INT | MIG | INT | MIG | INT | MIG | INT | MIG | INT |
| 0.007 | 0 | 0 | 0 | 0 | 0 | 0 | 0 | 0 | 0 | 0 | 0 | 0 | 1 | 1 |

LEGEND
MIG = Migration
INT = Intensity

With the addition of primaquine, similar results were thus observed. The control reagent was able to detect hemin at a concentration of 0.007 mg/g feces. In the presence of 0.05% primaquine, hemin was not detectable at concentrations of 0.007 or 0.15 mg/g feces.

Accordingly, by adding primaquine to the specimen, it is possible to construct a reagent capable of detecting fecal hemin only when a threshold of 0.03 mg hemin per ml had been reached.

C. Quinidine. The same procedures and reagents as in the previous two examples were used to test quinidine. Similar results were seen here. At a concentration of 0.05%, quinidine prevented detection of hemin in feces at a concentration of 0.007 mg/g feces. At 2% quinidine, no positive response was seen at 0.007 or 0.015 mg hemin/ml. A positive response in the presence of 2% quinidine was not reached until the fecal hemin concentration reached 0.03 mg/g feces.

TABLE 13

| | Quinidine Concentration | | | | | | | | | | | | | |
|---|---|---|---|---|---|---|---|---|---|---|---|---|---|---|
| | Reagent I 2.0% | | Reagent II 1.0% | | Reagent III 0.5% | | Reagent IV 0.2% | | Reagent V 0.1% | | Reagent VI .05% | | Reagent VIII Control | |
| Hemin mg/gram | MIG | INT | MIG | INT | MIG | INT | MIG | INT | MIG | INT | MIG | INT | MIG | INT |
| 0.24 | 10 | 10 | 10 | 10 | 10 | 10 | 10 | 10 | 10 | 10 | 10 | 10 | 10 | 10 |
| 0.12 | 5 | 4 | 5 | 5 | 6 | 7 | 7 | 8 | 6 | 8 | 6 | 8 | 9 | 8 |
| 0.06 | 4 | 4 | 5 | 5 | 5 | 7 | 5 | 7 | 5 | 7 | 7 | 7 | 9 | 7 |
| 0.03 | 2 | 1 | 2 | 1 | 2 | 2 | 2 | 2 | 2 | 2 | 2 | 2 | 8 | 3 |
| 0.015 | 0 | 0 | 0.5 | 0.5 | 0.5 | 0.5 | 0.5 | 0.5 | 0.5 | 0.5 | 0.5 | 0.5 | 2 | 1 |
| 0.007 | 0 | 0 | 0 | 0 | 0 | 0 | 0 | 0 | 0 | 0 | 0 | 0 | 1 | 1 |

"MIG", "INT" as in Table 11.

In sum, it is possible to add inhibitory antimalarial drugs to an FOBT reagent, thereby decreasing the sensitivity of the reagent. It is also possible to add the inhibitory antimalarials directly to the fecal specimen, thereby adjusting the sensitivity of the test reagent.

EXAMPLE 7

To reduce false positive test results caused by dietary meat ingestion, fecal specimens from 5 separate dogs consuming meat in the form of canned dog food were exposed to solvents containing quinidine prior to the addition of the FOBT reagent. All of the dogs were normal, and were free from intestinal helminths.

The following were used: Reagent I: 0.5% guaiac, 1% ABTS, 1.8% DACHTAA, 1.5% chloroquine, 5% CHP in 70% TMU/ 30% DEA 1M, pH 7.0; Reagent II: 1% ABTS, 1.8% DACHTAA, 0% quinidine in 70% TMU/30% DEA 1M, pH 7.0; Reagent III: Same as Reagent II, except 5% quinidine; and Reagent IV: 1% guaiac, 10% CHP, 1% ABTS, 1.8% DACHTAA, 3% chloroquine in 70% TMU/30% DEA 1M, pH 7.0, note: Reagents I and IV both contain chloroquine.

Procedure: Dog #1 and Dog #2 had a meat diet consisting of ½ can Kal Can brand meat flavored dog food mixed with 3 cups Iams Chunks dry dog food per day. Dog #3 had a diet consisting of 2-3 cups Wayne dried dog food and irregular, but frequent table scraps. Dogs #456 and #474 were kennel animals free from intestinal parasites, and maintained on a mixed meat/dry dog food diet.

Fecal smears of the canine samples were made on Whatman #1 filter paper and allowed to dry at room temperature. Twenty microliters of Reagent II and III was added over the fecal smears. Twenty microliters of 0.5% guaiac Reagent I was then added to the fecal spots (smears) on Column 1 and twenty microliters of the 1% guaiac Reagent IV was then added to the fecal spots on Column 2 and 3. The color intensity and migration were determined at 1, 2, and 5 minutes. (Legend: Color Intensity: 0=no perceptible blue color; +1=barely perceptible blue color; +10=intense, solid blue color; intermediate ratings=blue color of intermediate intensity. Color Migration: 0=no color migration, color is formed, but fails to move from the catalyst spot; 10=complete movement of color from the specimen to the solvent front; intermediate ratings=movement of color between solvent front and the catalyst spot.)

The specimens were smeared onto untreated filter paper and then either tested with a prototype FOBT directly, or treated with solvent alone, or with solvent containing quinidine before exposure to the FOBT reagent. The concentrations and volumes of components were adjusted such that the final concentration of guaiac and cumene hydroperoxide present during the final FOBT incubation were essentially the same in all cases.

In the first experiment (Table 14) the specimens were tested in the absence of chloroquine except for those in column 1 when chloroquine was present. All of the specimens tested in this experiment produced a color. When chloroquine was present, color formation was more intense and appeared very quickly. 5% quinidine almost completely prevented color formation with the FOBT reagent lacking chloroquine. This was true whether test readings were made at one or five minutes.

The experiment was repeated with FOBT reagents containing chloroquine (Table 15). In this case, the rate and extent of color formation was very similar whether the complete FOBT reagent was added to the specimen, or formed by mixing solvent and concentrated reagent at the specimen site itself. Specimens pretreated with quinidine produced much less color than their untreated counterparts, and two of the fecal specimens (from dogs 3 and 456) produced no color whatever. The remaining three specimens produced only the faintest color still discernable visually in the test system employed. Thus, by pretreating fecal specimens from dogs ingesting meat with quinidine, it was possible to reduce false positive FOBT test results caused by meat ingestion.

TABLE 14

| Sample | Time | Column 1 Reagent I Control | | Column 2 Reagent II 0% Quinidine | | Column 3 Reagent III 5% Quinidine | |
|---|---|---|---|---|---|---|---|
| | | MIG | INT | MIG | INT | MIG | INT |
| Dog #1 | 1 min | 10 | 8 | 8 | 2 | 0 | 0 |
| | 5 min | — | — | 8 | 5 | 0 | 0.5 |
| Dog #2 | 1 min | 10 | 7 | 8 | 2 | 0 | 0 |
| | 5 min | — | — | 7 | 3 | 0 | 0 |
| Dog #3 | 1 min | 10 | 5 | 2 | 1 | 0 | 0 |
| | 5 min | — | — | 5 | 3 | 0 | 0 |
| Dog #456 | 1 min | 10 | 7 | 3 | 1 | 0 | 0 |
| | 5 min | — | — | 5 | 3 | 0 | 0 |
| Dog #474 | 1 min | 10 | 7 | 3 | 1 | 0 | 0 |
| | 5 min | — | — | 5 | 3 | 0 | 0 |

"MIG", "INT" as in Table 11.

TABLE 15

| Sample | Time | Column 1 Reagent I Control | | Column 2 Reagent II 0% Quinidine | | Column 3 Reagent III 5% Quinidine | |
|---|---|---|---|---|---|---|---|
| | | MIG | INT | MIG | INT | MIG | INT |
| Dog #1 | 1 min | 10 | 9 | 10 | 9 | 2 | 1 |
| Dog #2 | 1 min | 10 | 9 | 10 | 9 | 2 | 1 |
| Dog #3 | 1 min | 10 | 5 | 10 | 5 | 0 | 0 |
| Dog #456 | 1 min | 9 | 8 | 10 | 8 | 0 | 0 |
| Dog #474 | 1 min | 9 | 9 | 10 | 9 | 2 | 1 |

"MIG", "INT" as in Table 11.

What is claimed is:

1. A developer composition for detecting iron protoporphyrins in a fecal specimen using a leuco dye indicator, comprising a solution of a hydroperoxide and a modulating compound, wherein he solution contains at least 50% by volume of a solvent for iron protoporphyrins, and wherein the modulating compound is an accelerator selected from the group consisting of chloroquine, quinacrine and mixtures thereof.

2. The developer composition method of claim 1, wherein the accelerator is chloroquine.

3. The developer composition of claim 1, wherein the accelerator is quinacrine.

4. The developer composition of claim 1, wherein the hydroperoxide is selected from the group consisting of hydrogen peroxide, cumene hydroperoxide, t-butyl hydroperoxide, diisopropylbenzene hydroperoxide, and 2,5-dimethylhexane hydroperoxide.

5. A developer composition for detecting iron protoporphyrins in a fecal specimen using a leuco dye indicator, comprising a solution of a hydroperoxide and a modulating compound, wherein the solution contains at least 50% by volume of a solvent for iron protoporphyrins, and wherein the modulating compound is an inhibitor selected from the group consisting of quinien, primaquine, quinidine, and mixtures thereof.

6. The developer composition of claim 5, wherein the inhibitor is quinine.

7. The developer composition of claim 5, wherein the inhibitor is primaquine.

8. The developer composition of claim 5, wherein the inhibitor is quinidine.

9. The developer composition of claim 5, wherein the hydroperoxide is selected form the group consisting of hydrogen peroxide, cumene hydroperoxide, t-butyl hydroperoxide, diisopropylbenzene hydroperoxide, and 2,5-dimethylhexane hydroperoxide.

10. A developer composition for detecting iron protoporphyrins in a fecal specimen using a leuco dye indicator, comprising a solution of a hydroperoxide, an accelerator selected from the group consisting of chloroquine, quinacrine, and mixtures thereof, and an inhibitor selected from the group consisting of quinine, primaquine, quinidine, and mixtures thereof, wherein the solution contains at least 50% by volume of a solvent for iron protoporphyrins.

11. The developer composition of claim 10, wherein the hydroperoxide is selected form the group consisting of hydrogen peroxide, cumene hydroperoxide, t-butyl hydroperoxide, diisopropylbenzene hydroperoxide, and 2,5-dimethylhexane hydroperoxide.

12. The developer composition of any one of claims 1, 5 or 10, wherein the solvent for iron protoporphyrins is (a) an amide of the formula

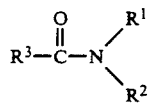

wherein $R^1$, $R^2$, and $R^3$ are the same or different and represent hydrogen, lower alkyl, phenyl or benzyl, with the provisos that both of $R^1$ and $R^2$ are not hydrogen and $R^3$ may be linked with $R^1$ or $R^2$ to form a 5- or 6-membered heterocycle;

(b) a sulfoxide or sulfone of the formula

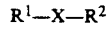

wherein X is

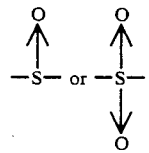

and $R^1$ and $R^2$ are the same or different and are lower alkyl, phenyl or benzyl, or, when X is

$R^1$ and $R^2$ may be linked to form a 5- or 6-membered heterocycle;

(c) pyridine;

(d) a mixture of ethanolamine or dimethylamine and a co-solvent selected from the group consisting of methyl ethyl ketone, tetramethylene sulfone, butyrolactone, tetrahydrofurfuryl alcohol, 2-methoxy ethanol, and tetramethyl urea;

(e) a mixture of 2-(diethylamino)ethylamine and a cosolvent selected from the group consisting of methyl ethyl ketone, acetonitriles, tetramethylene sulfone, butyrolactone, tetrahydrofurfuryl alcohol, 2-methoxy ethanol, and methanol; or (f) a mixture of diethanolamine and a co-solvent selected from the group consisting of methyl ethyl ketone, acetonitrile, tetramethylene sulfone, butyrolactone, and tetrahydrofurfuryl alcohol.

13. The developer composition of claim 12, wherein the solvent for iron protoporphyrins is an amide having the formula

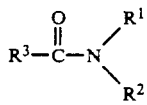

wherein $R^1$, $R^2$ and $R^3$ are the same or different and represent hydrogen, lower alkyl, phenyl or benzyl, with the provisos that both of $R^1$ and $R^2$ ar not hydrogen and $R^3$ may be linked with $R^1$ or $R^2$ to form a 5- or 6-membered heterocycle.

14. The developer composition of claim 12, wherein the solvent for iron protoporphyrins is a sulfoxide or sulfone of the formula $$R^1-X-R^2$$

wherein X is

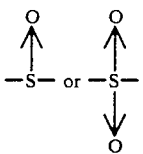

and $R^1$ and $R^2$ are the same or different and are lower alkyl, phenyl or benzyl, or, when X is

$R^1$ and $R^2$ may be linked to form a 5- or 6-membered heterocycle.

15. The developer composition of claim 12, wherein the solvent for iron protoporphyrins is pyridine.

16. The developer composition of claim 12, wherein the solvent for iron protoporphyrins is a mixture of ethanolamine or dimethylamine and a co-solvent selected form the group consisting of methyl ethyl ketone, tetramethylene sulfone, butyrolactone, tetrahydrofurfuryl alcohol, 2-methoxy ethanol, and tetramethyl urea.

17. The developer composition of claim 12, wherein the solvent for iron protoporphyrins is a mixture of 2-(diethylamino)ethylamine and a co-solvent selected from the group consisting of methyl ethyl ketone, acetonitriles, tetramethylene sulfone, butyrolactone, tetrahydrofurfuryl alcohol, 2-methoxy ethanol, and methanol.

18. The developer composition of claim 12, wherein the solvent for iron protoporphyrins is a mixture of diethanolamine and a co-solvent selected from the group consisting of methyl ethyl ketone, acetonitrile, tetra methylene sulfone, butyrolactone, and tetrahydrofurfuryl alcohol.

* * * * *